United States Patent [19]

Vilmar

[11] Patent Number: 5,156,590
[45] Date of Patent: Oct. 20, 1992

[54] URETERO-RENOSCOPE WITH CATHETER BODY HAVING PLURAL PARTITIONED INNER CONDUITS

[76] Inventor: Wolfgang Vilmar, Valznerweiherstrasse 84, 8500 Nurenberg 30, Fed. Rep. of Germany

[21] Appl. No.: 719,438

[22] Filed: Jun. 24, 1991

[51] Int. Cl.⁵ .................................................. A61B 1/00
[52] U.S. Cl. .................................................. 604/4; 604/6
[58] Field of Search ................................... 128/4, 6, 7

[56] References Cited

U.S. PATENT DOCUMENTS

| | | | |
|---|---|---|---|
| 4,576,145 | 3/1986 | Tsuno et al. | 128/6 |
| 4,576,146 | 3/1986 | Kawazoe et al. | 128/6 |
| 4,688,554 | 8/1987 | Habib | 128/4 |
| 4,756,303 | 7/1988 | Kawashima et al. | 128/6 |
| 4,919,112 | 4/1990 | Siegmund | 128/6 X |

FOREIGN PATENT DOCUMENTS 2157017 10/1985 United Kingdom .................... 128/4

Primary Examiner—John J. Wilson
Assistant Examiner—Jeffrey A. Smith
Attorney, Agent, or Firm—Browdy and Neimark

[57] ABSTRACT

An endoscope, particularly for use as a uretero-renoscope, includes a catheter head piece with a flexible catheter body in the form of a semi-flexible hose having a highly flexible tip, the hose being divided into internal axially extending conduits by interior walls which bisect the interior of the catheter body in as asymmetric fashion so that the conduits are not of equal size. The head piece is in the form of an ergonimcally shaped rod-like handle which surrounds an eye piece and is disclosed coaxial with the catheter body.

16 Claims, 5 Drawing Sheets

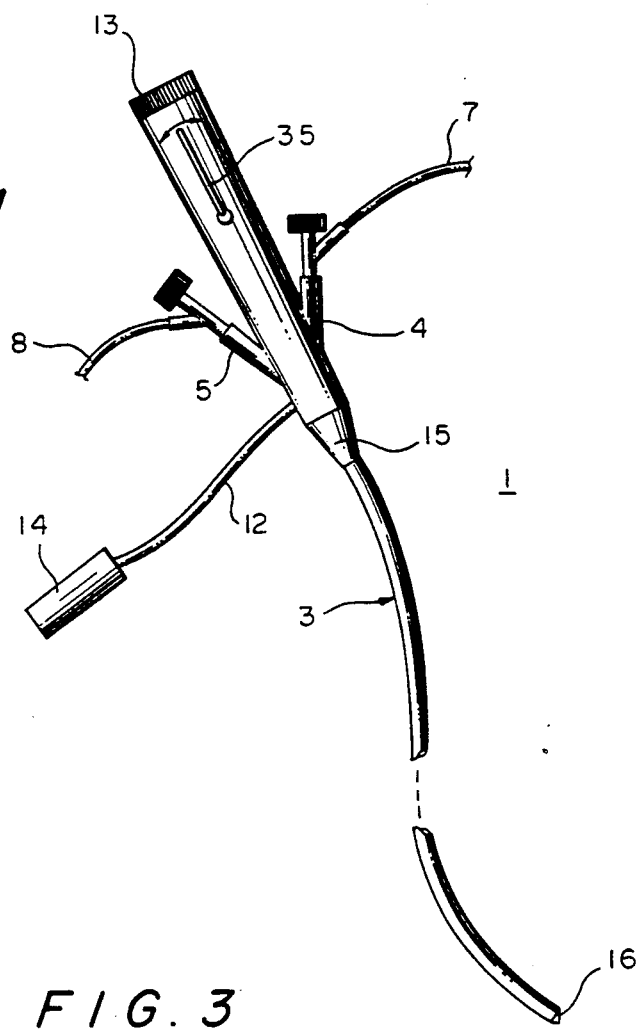
FIG. 1
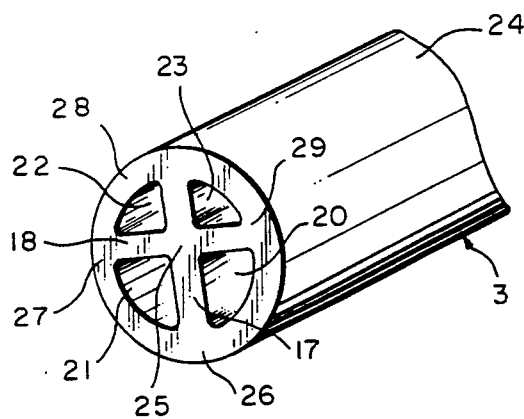
FIG. 3
FIG. 2

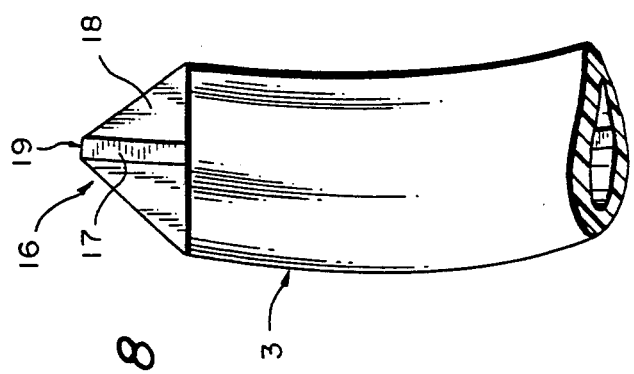
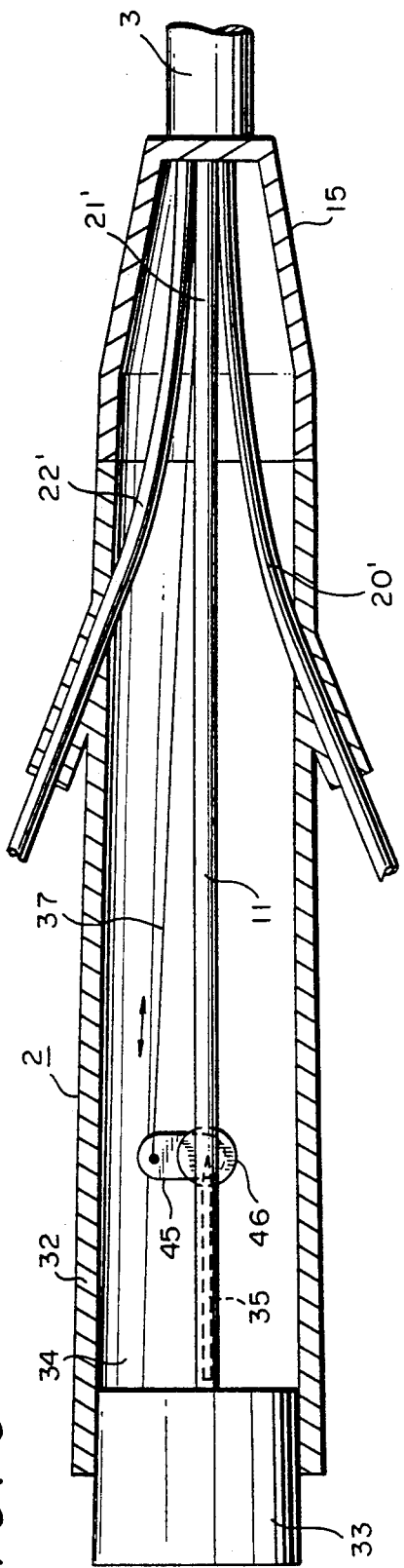
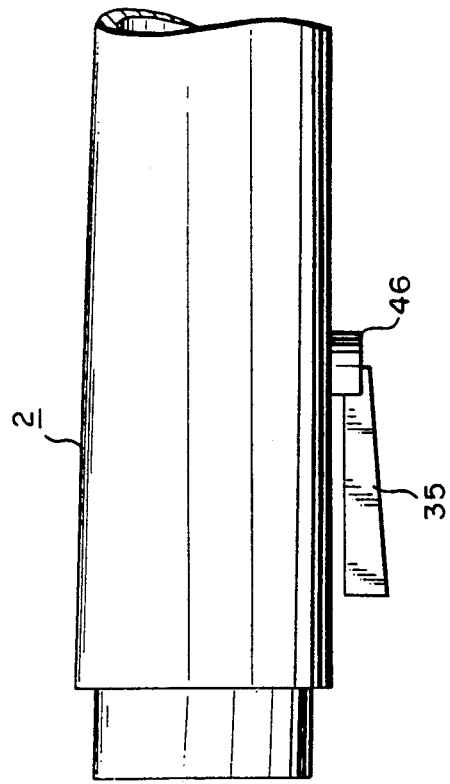

URETERO-RENOSCOPE WITH CATHETER BODY HAVING PLURAL PARTITIONED INNER CONDUITS

FIELD OF THE INVENTION

The invention relates to an endoscope, more particularly an uretero-renoscope, essentially comprising a catheter head piece with a flexible catheter body embodied in the shape of a hose attached thereto, which has a number of conduits, one of which is used as an optical conduit which contains an optical waveguide making observation possible, and further conduits which are used either as working conduits through which in particular operating instruments (for example a laser optic fiber) are fed or as irrigation conduits for conducting irrigation liquids.

BACKGROUND

Such uretero-renoscopes are used in connection with rigid catheter bodies which are disadvantageous in several respects. They have a diameter requiring treatment of the ureter with a so-called bougie, i.e. reaming, which requires in-hospital pre-treatment of the patient for two to three days and, after treatment, a hospital stay of one to two weeks. Furthermore, such renoscopes must be used with the aid of X-ray equipment and anesthesia of the patient, because otherwise the treatment cannot be endured by the patient.

The known uretero-renoscopes are furthermore not satisfactory, because they have too few conduits, their diameter is relatively large and the flexibility of the catheter is insufficient to assure a really problem-free insertion into the ureter at the critical points. However, the result, if a plurality of conduits are used, is that the manipulation of the renoscope in the working area of the examining physician, i.e. in the area of the catheter head piece, leaves much to be desired.

SUMMARY AND GENERAL DESCRIPTION

It is therefore an object of the invention to improve a flexible uretero-renoscope offering a multitude of operating and diagnostic possibilities, which for example can also be used on an outpatient basis, is maintenance-free and repeatedly usable, and where the catheter body has sufficient rigidity balanced with flexibility so as to be guided through narrowed places in the ureter in such a way that it assures the highest degree of comfortable manipulation even under the most difficult conditions.

This object is achieved by making the catheter head piece as an ergonomically shaped, rod-like handle, which surrounds an eye piece and is disposed in the axial extension of the catheter body.

Due to the fact that the handle is disposed in the axial extension of the catheter body, it is possible in a simple manner to transfer all conduits of the catheter body into the handle, and every conduit can be assigned a particular place on the handle independently of the others. In this way the examining physician is able to grasp the renoscope by the handle with one hand and to follow the examination or operation through the observation tube or the eye piece, and with the other hand he can perform all tasks, such as irrigation of the examined location and/or performing a laser cut. The invention has the advantage that the ease of manipulation of the renoscope according to the invention does not decrease with added numbers of conduits.

The decisive part is that all conduit-related connections as well as the actuation elements connected therewith, such as cocks, levers or the like, are located directly, but separated from each other, on the rod-like handle.

In a suitable manner the observation tube or the eye piece are integrated into the front face of the end of the handle facing away from the catheter body. This also results in good handling characteristics.

In accordance with a further embodiment of the invention, the handle is connected with a catheter body which embodies at least four conduits. One conduit of the four contains the fiber optics, while the others can be used selectively as separate irrigation conduits and/or working conduits. In accordance with the invention, all connecting elements as well as connecting lines for the conduits are located in the area of the tip of the handle facing the patient, so that a wide and uncluttered handle area is created. In this case the connecting elements and/or connecting lines can be disposed symmetrically to the center axis of the handle.

To form these conduits, the catheter body is formed with an essentially round interior cross section, where two essentially vertically intersecting partitions are provided and three free conduits are thus formed, which can be used selectively as separate irrigation conduits and/or working conduits. The fourth conduit contains the fiber optics.

The partitions have a dual function in that they not only provide the separation of the conduits, but they also provide the catheter body with a virtually optimal rigidity, without the catheter body becoming too inflexible to be guided through difficult passages of the ureteral tract. In this regard, the catheter body is suitably made of a flexible plastic material, and the partitions serve as structural reinforcement.

If an intersecting point of the two partitions is disposed eccentric in relation to the catheter body cross section, the result is not only an advantageous division of the cross section of the conduits, but a certain asymmetry or anisotropy of the resilient properties of the catheter body, which can be advantageously employed when placing the catheter body into difficult ureter passages.

It is furthermore advantageous if the the working conduit is formed by one of the free conduits of large cross section. It is possible, in particular for surgical laser purposes, to guide a laser fiber through this working conduit. In general the conduits of greater cross section can be used as working conduits in an advantageous manner.

For example, there is the advantageous possibility of guiding the laser fiber, provided it is made sufficiently thin, through one working conduit formed by one of the free conduits, while another one of the free conduits is then available for at least one irrigation conduit, which assures highly efficient irrigation. In this way there is free selectivity with respect to the free conduits.

To assure the separated disposition of the individual conduit outlets in the handle, it is useful to provide conduits in the handle which correspond to the individual conduits of the catheter body.

To provide quick connection or a quick interchange between handle and catheter body, the handle and the catheter body are removably connected with each other by means of a connecting arrangement. This connecting arrangement may be, for example, a handle tip, which receives the catheter body and additionally can be removably connected with the actual handle via a screw connection. This has the advantage that the interior of the handle is very conveniently accessible by means of the removable handle tip on the side of the handle facing the patient. However, alternatively, it is also useful to provide that the handle and the catheter body are made of one piece. This provides the opportunity to make the handle and the catheter body in one piece during one manufacturing step, particularly if both parts are made of plastic.

A particular advantage is achieved by means of a Bowden control or wire which extends from a place disposed on the handle through the handle and the catheter body to the tip of the catheter body, and engages the end of the Bowden control eccentrically in the tip area, so that the tip area is pivotable in relation to the remaining catheter body by means of an axial movement of the Bowden control. In this way, the catheter body can be moved and in particular bent in a purposeful way in the area of its tip facing away from the catheter head piece. The Bowden control is available for this purpose, which is run through the catheter body as far as its tip area, preferably essentially parallel to the optical conduit and the other free conduits in the catheter body which are used as irrigation conduits and/or working conduits.

With the aid of this Bowden control it is possible, for example, for the operating physician to bend the area of the tip of the catheter body, inserted through the ureter and into a kidney, carefully and discriminately, in case such a step is helpful or required.

A useful improvement consists in an area of the tip or end section of the catheter body, having a predetermined length and extending to the tip, being movable and in particular bendable. This is achieved in a particularly useful manner in that the tip area or the end section have a degree of flexibility, i.e. mobility, which is increased in relation to the remaining catheter body.

Because the Bowden control can be moved in the axial direction by means of a manipulator directly connected with the handle, it is possible in an advantageous manner to achieve curving of the tip area or end section of the catheter body.

In a useful way the mobility of the tip area is in a range of at least 90° in relation to the orientation of the catheter body.

In an advantageous manner the manipulator for the axial operation of the Bowden control and thus the movement of the tip area of the catheter body is disposed directly on the handle, namely within the gripping area of the handle. The physician can hold the handle with one hand, and with the same hand he can operate the Bowden control with the manipulator if, in accordance with a further embodiment of the invention, the manipulator is embodied as a pivotable lever, which can be moved by finger pressure crosswise to the longitudinal axis of the handle. The second hand is then completely free for manipulations at the conduit outlets. For insertion of the Bowden control, i.e. the wire, as far as the catheter body tip, a central conduit is usefully provided in the catheter body.

A wire or cable with high flexibility should be preferably used.

BRIEF DESCRIPTION OF THE DRAWINGS

The attached description of exemplary embodiments in connection with the drawings is used for the detailed explanation of the invention, its further characteristics and advantages, wherein FIG. 1 is a schematic view of an uretero-renoscope according to the present invention;

FIG. 2 is a schematic cross section of a catheter body embodied in a hose-like manner in an enlarged view;

FIG. 3 is a perspective view of an end section of the catheter body in an enlarged view;

FIG. 6 is a schematic axial sectional view of the catheter head piece embodied as handle, with the catheter body connected;

FIG. 7 shows the gripping area of the handle with a manipulator for actuating the renoscope tips;

FIG. 8 is a lateral view of the end section of the catheter body containing the catheter tip;

DETAILED DESCRIPTION OF THE EMBODIMENTS

Figure 4:
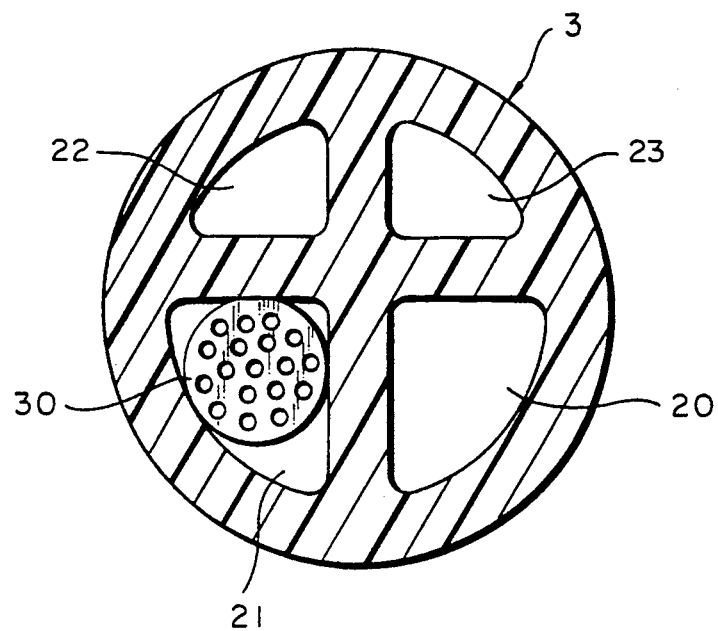
FIG. 4 is an enlarged cross section of the catheter body in accordance with FIG. 3 with the fiber optics inserted.

As indicated in FIG. 1, the uretero-endoscope 1 in accordance with the invention comprises a catheter head piece in the shape of an elongated, rod-like handle 2 having a shape which is particularly handy for the treating physician, i.e. ergonomical.

At its pointed end, the handle 2 is connected in the axial direction with a flexible catheter body 3 embodied in a hose-like manner, which is inserted into the end of the handle 2. The end of the handle comprises a handle tip 15 as a separate part to provide a connection between the catheter body 3 and the handle 2 and to make the interior of the handle 2 easily accessible. The connection between the handle tip 15 and the handle 2 can be made in a simple manner by screwing or the like.

On its cylindrical or cone-shaped exterior, the handle 2 has a first connector element 4, a second connector element 5 and a third connector element located on the back and therefore not shown. A first connecting line 7, a second connecting line 8 and a third connecting line, not shown, can be removably connected with these connector elements. All of the connector elements are separately disposed directly on the handle 2.

In FIG. 1 the connector elements are symmetrically disposed around the exterior of the handle 2 in relation to the axial direction or the longitudinal axis of the handle 2. The observation tube or the eye piece 13 are disposed on the end of the handle facing away from the patient. A gripping area for holding the handle 2 is disposed between the connector elements and the end of the handle 2 facing away from the patient.

The observation tube comprises an eye piece 13 connected with the fiber optics extending beyond the catheter body 3 (not shown in FIG. 1). The fiber optics are realized by light-conducting fiberglass bundles brought together in the interior of the handle 2. The fiberglass bundles of a branch line 12 connected with a light source 14 conduct light to the tip area of the catheter and illuminate the places to be examined. The image at the tip of the catheter body 3 is brought to the eye piece 13 of the observation tube via a further light-conducting fiberglass bundle. Both fiberglass bundles run through the optical conduit. The optical conduit branches inside the handle 2 into a first branch line 11 leading to the eye piece 13 (see FIG. 6) and a second branch line 12. Both the first and second branch lines 11 and 12 are of course flexible.

In the uretero-endoscope illustrated in FIG. 1, the handle 2 and catheter body 3 (including the connecting line disposed on the back) are provided with four conduits. However, in connection with other embodiments it is possible, if required, to have a number of conduits in excess of four conduits.

A schematic cross section of the catheter body 3 embodied in a hose-like manner is shown in FIG. 2. Essentially, it has a round cross section and is provided on the inside with two partitions, essentially crossing at right angles, namely a first partition 17 and a second partition 18 forming a common crossing 19. As a result, four conduits separated from each other are formed in the interior of the catheter body 3, i.e. a first conduit 20, a second conduit 21, a third conduit 22, and a fourth conduit 23.

The embodiment just described can also be seen from FIG. 3, which is preferably formed of a plastic material such as polyurethane. It is essential in connection with this embodiment of the catheter body 3 that its first and second partitions 17 and 18 are disposed in such a way that the crossing 19 of the partitions 17 and 18 is located eccentrically in respect to the cross section of the catheter body 3. As a result there are two conduits each with a larger cross section, these being the first and second conduits 20 and 21, and two conduits each with a narrower cross section, these being the third and fourth conduits 22 and 23

In this way, two of the conduits have approximately the same cross section and thus constitute, the first and second conduits 20 and 21 of equal and larger cross section, and the third and fourth conduits 22 and 23 of equal and smaller cross sections. The ratio of the cross sections of the larger conduits to the cross sections of the narrower conduits preferably is approximately 3:1.

As shown in particular by FIGS. 3 and 4, the first and second partitions 17 and 18 each have in the area of their (crossing 19 in accordance with FIG. 2), as well as in the area of their transition into an exterior wall 24 of the catheter body 3, enlargements 25, 26, 27, 28 and 29, which serve as stiffeners by means of which the inherent stability of the catheter body 3 is increased.

The uretero-endoscope discussed in the exemplary embodiments thus has a total of four conduits as already mentioned, the first conduit 20 being a working conduit, the second conduit 21 being the optical conduit already mentioned above, the third conduit 22 being a separate inlet irrigation conduit and the fourth conduit 23 also being a separate outlet irrigation conduit. As shown in particular in FIGS. 4 and 5, the fiber optics bundle 30 consisting of the branch lines 11 and 12, runs through the second conduit 21, i.e. the optical conduit. In a known manner it consists of a light-conducting fiberglass bundle, such as has already been used in connection with known fiber optics endoscopes.

Figure 5:
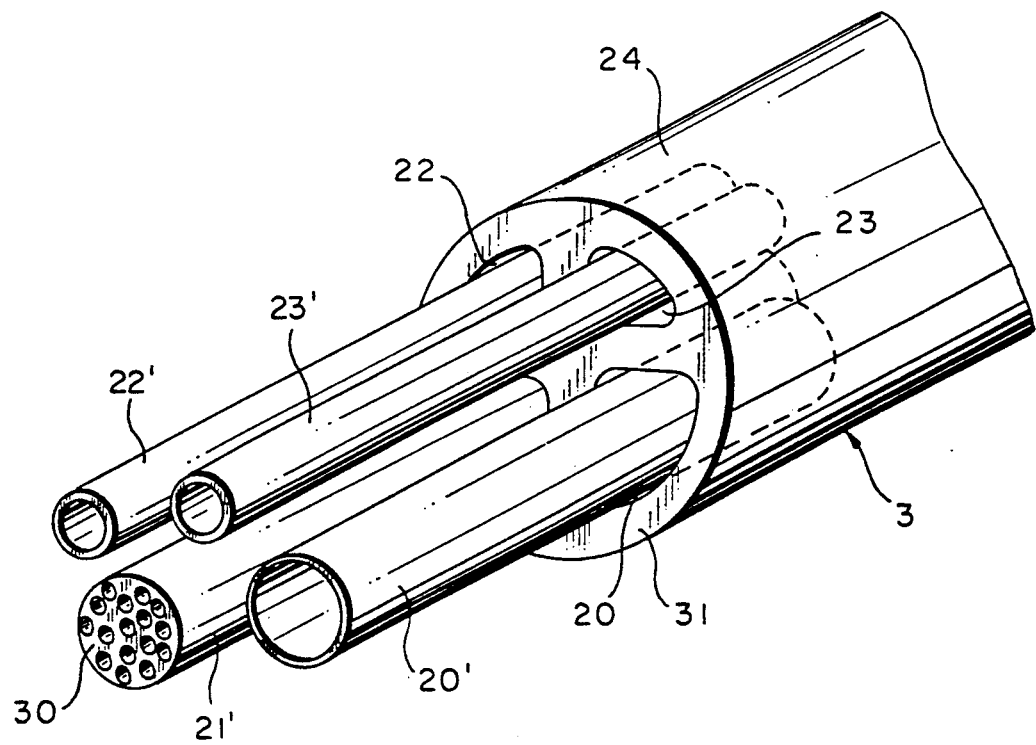
FIG. 5 is a perspective view of a section of the catheter body with one of the continuation conduits connected to its end.

A front end 31 of the four-conduit catheter body 3 embodied in the shape of a hose is shown in FIG. 5. As can be there seen, four continuation conduits 20', 21', 22' and 23' are provided for the realization of the appropriate four-conduit embodiment of the handle 2. They are connected to the catheter body 3 in the area of its front end 31. This front end 31 is that end which is usefully employed for connecting the handle tip 15 of the handle 2 (see FIG. 1).

In this connection, the first continuation conduit 20' is associated with the first conduit 20 (the working conduit), the second continuation conduit 21' with the second conduit 21 (the optical conduit), the third continuation conduit 22' with the third conduit 22, i.e. the first irrigation conduit and, finally, the fourth continuation conduit 23' with the fourth conduit 23, i.e. the second irrigation conduit.

In FIG. 5, the described four continuation conduits 20' to 23' are each shown with their ends cut off. Actually, these continuation conduits extend continuously to the handle 2 connected with the front end 31 of the catheter body 3, as shown in detail in FIG. 6, which essentially illustrates an axial sectional view of the handle 2. The essentially rod-shaped handle 2 has a casing 32 and a cover part 33, which is rotatably seated and permits focusing of the eye piece.

An interior chamber 34 of the handle 2 is defined by the conical handle casing 32 and the cover part 33, which is entered by the continuation conduits, for example 20' to 22', coming out of the catheter body 3. For the sake of clarity, in FIG. 6 only the course of the first continuation conduit 20', the second continuation conduit 21' and the third continuation conduit 22' are shown. The second continuation conduit 21' with the fiber optics 30 disposed therein represents a conduit with a larger cross section and extends, as shown in FIG. 6, without bending and in an axial direction through the handle 2. Only in the upper area of the handle 2 does it branch off into a first branch line 11, and into a second branch line 12 in the area of the handle tip 15 for leading the branch line 12 out. In the illustration according to FIG. 6, this branching is located at the back of the handle 2 and therefore cannot be seen.

As already mentioned, the handle 2 has a handle tip 15, which is preferably removably connected with the handle 2, for example by means of a threaded connection, not shown. This eases the insertion of the continuation conduits, of which the continuation conduits 20', 21' and 22' are shown in FIG. 6. In FIG. 6, a wire 37 is furthermore visible which, together with the continuation conduits 20' to 23', extends through the catheter body 3 and ends at the tip or in the tip area of the catheter body 3. The purpose of this wire 37 will be explained later. It can furthermore be seen in FIG. 6 that on its end located in the handle 2 the wire 37 is connected to a protrusion 45 engaged to pivot pin 46, which can be pivoted by means of a manipulator. Pivoting of the manipulator accordingly causes an axial displacement of the wire 37.

The gripping area of the handle 47 in accordance with FIG. 6 is shown in a lateral view in FIG. 7. In the area of the gripping portion of the handle 47, i.e. above the individual connector elements, the manipulator for actuation of the wire 37 or of the Bowden control is located, having the form of an elongated lever 35, extending essentially parallel to the handle 2. This arrangement makes it possible in a simple manner for the physician to actuate the lever with the same hand in which he holds the renoscope 1. In this way the second hand of the physician remains free for actuating laser pulses via a working conduit or to perform irrigations.

Finally, in FIG. 8 it can be seen that the tip 16 of the catheter body 3 is shaped to a conical configuration, e.g. by grinding, namely actually eccentrically ground on to the end and is conical in such a way that the intersection 19 of the two partitions 17 and 18 forms this ground-on tip.

It should also be mentioned that it is possible to connect selectively to the connector elements 4 and 5, and to a further connector element (not shown), provided on the exterior of the handle 2, the connecting lines 7 and 8 (see FIG. 1) and a further connecting line (not shown), depending on the manner in which the associated conduits are intended to be used, i.e. selectively as two separate irrigation conduits and as one working conduit, as already described in detail above.

Figure 9:
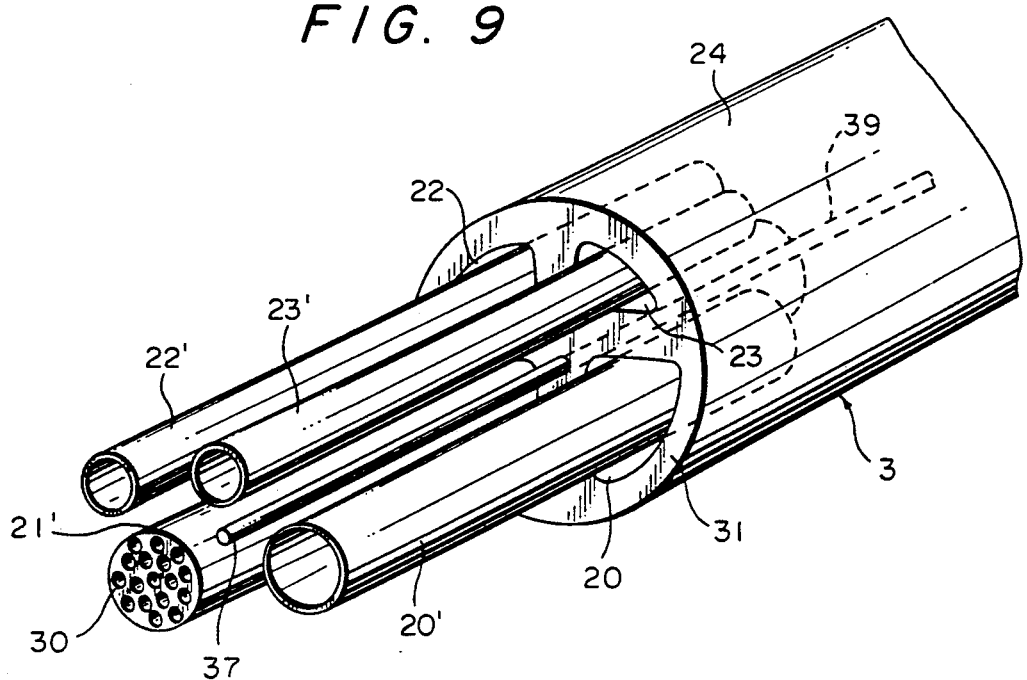
FIG. 9 is a perspective view of a section of the catheter body of the uretero-renoscope in an enlarged view.

As shown in particular in FIG. 9, a preferably central conduit 39 is provided in the catheter body 3 of the uretero-renoscope 1, which is used for the insertion of the wire 37 for remote actuation, which is led through the catheter body 3 as far as its tip 16 and with its end is then connected in any suitable manner with this tip 16.

Figure 10:
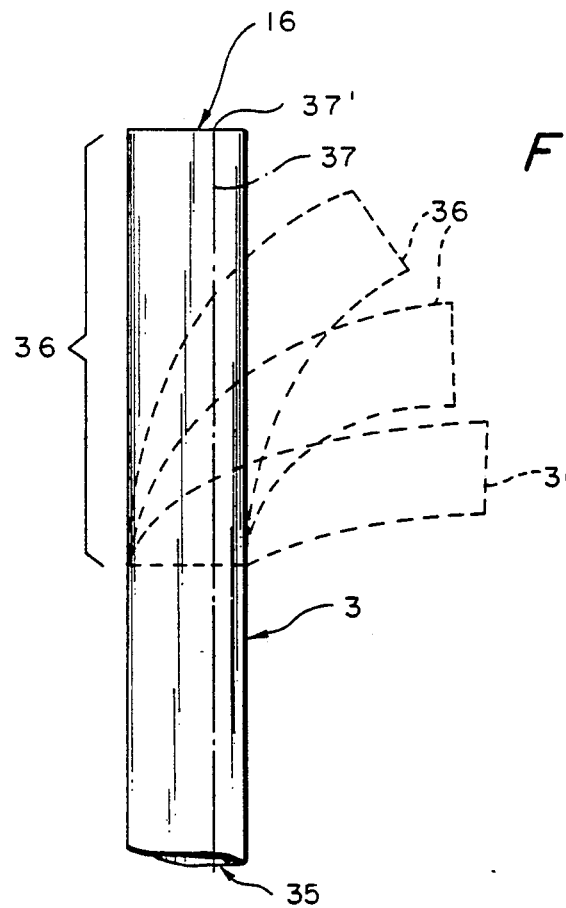
FIG. 10 is a schematic lateral view of the catheter body with its end section having increased flexibility containing the catheter tip, particularly for the embodiment of the uretero-renoscope in accordance with FIG. 9.

As particularly shown by FIG. 10, the tip area or end section 36, having for example a length of 4 cm, can be moved over an arc of approximately 90° with the aid of the wire 37. Preferably, this end section 36 consists of a material of greater flexibility than the remaining portion of the catheter body 3. In particular, it is possible to use relatively soft polyurethane for this end section 36, while the remaining portion of the catheter body 3 consists of relatively more rigid polyurethane. When the doctor or, operating physician operates the manipulator provided on on the handle 47, it is possible to bend the end section 36 with the tip there in a careful and discriminating manner, as illustrated in FIG. 10 by the various bent positions of the more highly flexible end section 36, shown by dashed lines.

A further exemplary embodiment of a catheter body 3 ensues from FIG. 11, in which again only the movable or bendable end section 36 of the catheter body 3 is shown. In this case the end section 36 has on its extreme end a relatively short sleeve 40, preferably a metal sleeve, which intimately encloses the end of the end section 36 and, in the other direction away from the tip 36, continues as a spiral 41, also preferably a metal spiral, which surrounds the remaining portion of the end section 36. The metal sleeve 40 with the resilient metal spiral 41 have the purpose to assure the desired flexibility of the end section 36.

Figure 11:
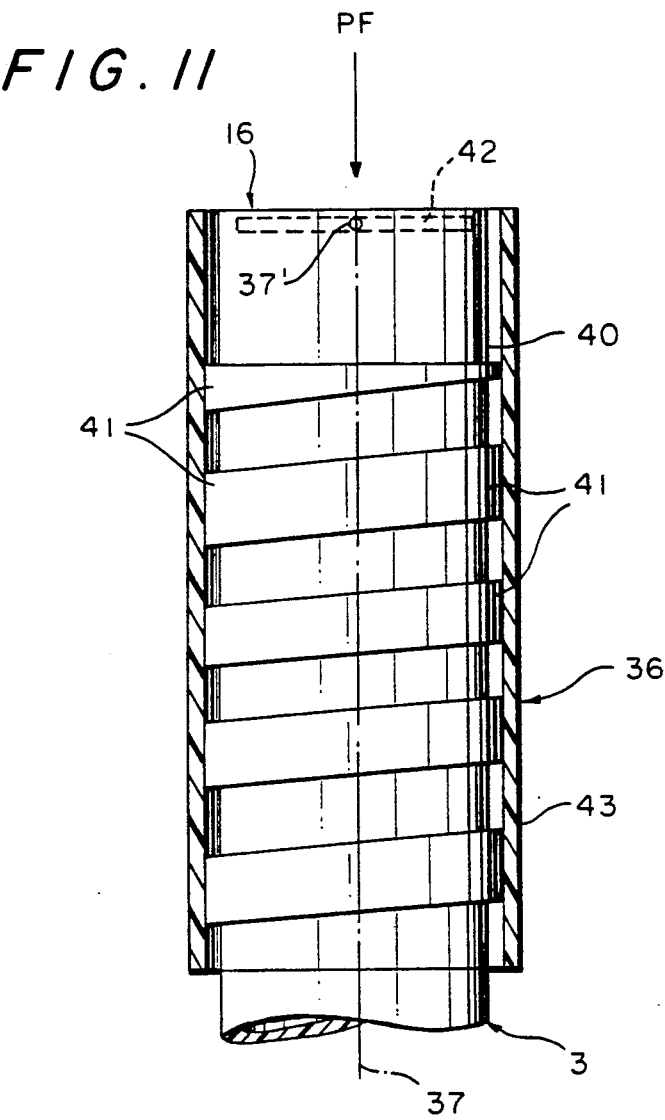
FIG. 11 is a lateral sectional view of a further exemplary embodiment of a catheter body with its movable or bendable end section containing the catheter tip.

Finally, FIG. 11 also shows that the entire bendable end section 36 of the catheter body 3, and in particular the metal sleeve 40 located there, together with the directly connected metal spiral 41, is surrounded by a plastic outer sleeve 43, which is particularly used for preventing friction in the area of the end section 36 of the catheter body 3.

Figure 12:
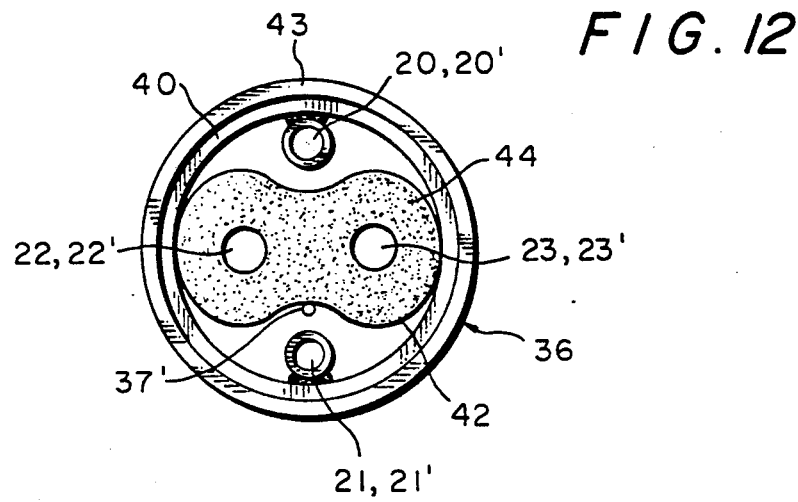
FIG. 12 is a top view of the tip of the catheter body in accordance with FIG. 11 in the direction of the arrow Pf.

Additionally, FIG. 12 discloses that the extreme end of the end section 36 containing the catheter tip 16 has an annular element, preferably a metal ring 42, which is inserted there into this extreme end and connected in a suitable manner with the inner wall of the end section 36. This metal ring is not in the form of a circle, but in the shape of a FIG. 8, i.e. with central indentations, as indicated by the top view of the catheter tip 16 in accordance with FIG. 12.

Two conduits 22 and 23 terminate inside this metal ring 42 with their respective continuation conduits 22' and 23', i.e. in the present exemplary embodiment a working conduit 22 for purposes of laser operations and an irrigation conduit 23. The ends of the two working and/or irrigation conduits 22 and 23 are fixed in the area of the metal ring 42 surrounding them, in particular by a fixing filler of plastic material for example by means of polyurethane foam 44.

It is furthermore provided that the further conduits 20 and 21 and their respective continuation conduits 20' and 21' terminate in the area of the extreme end of the end section 36, i.e. were the metal ring 42 is disposed. The ends of these conduits 20 and 21 are also fixed. Preferably the ends of the conduits 20 and 21 are located in the area between the metal ring 42 and the inner wall of the end section 36. In a preferred manner these ends are glued into the extreme end, by means of which their fastening is assured.

The above explained fixing of the ends of all conduits 20 to 23 or their continuation conduits 20' to 23' is necessary for moving or bending these conduits together with the end section 36.

In addition, FIG. 12 also shows that an eccentric engagement point or hinge point 37' for the wire 37 is provided on the metal ring 42 in order to achieve the required curvature of the end section 36 during actuation. In the present exemplary embodiment this engagement or hinge point 37' is provided in close vicinity to the conduit 21. The corresponding end of the wire or cable 37 preferably is welded directly to the metal ring 42.

The outer diameter of the end section 36 is, for example, 2.4 mm, while the diameter of the two conduits 22 and 23 is approximately 500 to 600 $\mu$m. These two conduits 22 and 23 are used, for example, as working conduits for inserting a laser fiber and as irrigation conduit, while the conduit 20 is used as a light conduit for illuminating purposes and the conduit 21 as optical conduit for observation purposes.

The assignment of the conduits 20', 21', 22' and 23' in accordance with FIG. 9 is modified in FIG. 12, i.e. the first continuation conduit 20' leads to the light conduit 20, the second continuation conduit 21' leads to the optical conduit 21, the third continuation conduit 22' to the working conduit 22 and the fourth continuation conduit 23' to the irrigation conduit 23.

The foregoing description of the specific embodiments will so fully reveal the general nature of the invention that others can, by applying current knowledge, readily modify and/or adapt for various applications such specific embodiments without departing from the generic concept, and, therefore, such adaptations and modifications should and are intended to be comprehended within the meaning and range of equivalents of the disclosed embodiments. It is to be understood that the phraseology or terminology employed herein is for the purpose of description and not of limitation.

What is claimed is:

1. An endoscope comprising;
    an ergonomically rodlike handle (47) on a catheter head piece (2), a first end of a flexible tubular catheter body (3) detachably engaged to said catheter head piece (2), said catheter body (3) having a circular cross section and at least four axially extending conduits (20, 21, 22, 23), said at least four axially extending conduits (20, 21, 22, 23) formed by two axially extending partitions (17, 18) intersecting at right angles at a point eccentric to said circular cross section of said catheter body (3), connector passages (20',21', 22', 23') opening on said head piece (2) separately communicating with said at least four axially extending conduits (20, 21, 22, 23), a first end of a tip (16) engaged to a second end of said catheter body (3), said at least four axially extending conduits extending to a free end of said tip, a first end of a single Bowden control wire (37) engaged on said handle (47), said control wire (37) extending through said catheter body (3) and eccentrically connected at a second end of said control wire to said free end of said tip (16), control means (35, 45, 46) on said handle (47) and connected to said single Bowden control wire (37) for axially moving said control wire (37), means associated with said tip for permitting said tip to flex relative to said second end of said catheter body (3) when said control means is actuated, one of said at least four axially extending conduits containing a light conducting fiberglass bundle (30), a connector passage of said connector passages communicating with said one of said at least four axially extending conduits containing said light conducting fiberglass bundle (30) having an eye piece on said handle (47), and the remaining conduits of said at least four axially extending conduits selectively used for working and irrigation conduits.

2. An endoscope in accordance with claim 1, wherein said eye piece (13) is integrated with the front of said end of the handle (47) facing away from the catheter body (3).

3. An endoscope in accordance with claim 1, wherein all said connector passages which are in communication with said conduits are located near the tip of the handle facing the patient, thereby providing a wide and uncluttered handle area (47).

4. An endoscope in accordance with claim 1, wherein said connector passages are disposed symmetrically around the center axis of said head piece (2).

5. An endoscope in accordance with claim 1, wherein said catheter body (3) is made of flexible plastic.

6. An endoscope in accordance with claim 1, wherein said catheter body (3) has a circular-cylindrical outer side wall connected by said two axially extending partitions (17, 18) which intersect and define therebetween with said sidewall said at least four axially extending conduits (20, 21, 22, 23), and wherein two conduits (20, 21) of said at least four axially extending conduits each has larger cross sections in comparison with the remaining conduits (22, 23).

7. An endoscope in accordance with claim 1, wherein said head piece (2) and the catheter body (3) are removably connected to each other by means of a connecting device in the form of a handle tip (15), which can be screwed on said head piece (2) and receives said first end of said catheter body (3).

8. An endoscope in accordance with claim 1, wherein said head piece (2) and the catheter body (3) are made in one piece.

9. An endoscope in accordance with claim 8, wherein said head piece (2) and the catheter body (3) are made of plastic.

10. An endoscope in accordance with claim 1, wherein said tip (16) of the catheter body (3) has greater flexibility than said catheter body.

11. An endoscope in accordance with claim 10, wherein said tip (16) is constructed to flex at least 90°.

12. An endoscope in accordance with claim 8, wherein said control means comprises a lever (35), pivotable crosswise to the longitudinal axis of said head piece (2), and disposed axially to said handle (47).

13. An endoscope in accordance with claim 1, wherein said head piece (2) contains a branch line (11) which carries a portion of said light conducting fiberglass bundle (30) to a light source (14) on said head piece (2).

14. An endoscope in accordance with claim 1, wherein an axially extending conduit (39), containing said single Bowden control wire (37), is provided in said catheter body (3) at the intersect of said interior walls.

15. An endoscope in accordance with claim 1, comprising a metal ring (42), inserted at said free end of said tip (16), said ring surrounding ends of two conduits (22, 23) of said at least four axially extending conduits used as said working and irrigation conduits, the ends of said two conduits (22, 23) fixed in the area of the ring (42).

16. An endoscope in accordance with claim 1, wherein said ends of said two conduits (22, 23) are molded into plastic.

* * * * *